(12) United States Patent
Lee et al.

(10) Patent No.: US 6,264,658 B1
(45) Date of Patent: Jul. 24, 2001

(54) SPINE FIXING APPARATUS

(75) Inventors: Choon Ki Lee, 6-506 Jin-ju Apt., Sinchun-dong, Songpa-ku, Seoul; Cheol Sang Kim, Chollabuk-do; Sung Pil Choi, Kyunggi-do, all of (KR)

(73) Assignees: Solco Surgical Instruments Co., Ltd., Kyunggi-do; Choon Ki Lee, Seoul, both of (KR)

( * ) Notice: Subject to any disclaimer, the term of this patent is extended or adjusted under 35 U.S.C. 154(b) by 0 days.

(21) Appl. No.: 09/347,836

(22) Filed: Jul. 2, 1999

(30) Foreign Application Priority Data

| Jul. 6, 1998 | (KR) | 98-27070 |
| Nov. 13, 1998 | (KR) | 98-48554 |
| Jun. 28, 1999 | (KR) | 99-25051 |

(51) Int. Cl.[7] .................................................. A61B 17/56
(52) U.S. Cl. ............................................................ 606/61
(58) Field of Search .............................. 606/61, 60, 69, 606/73, 72, 71

(56) References Cited

U.S. PATENT DOCUMENTS

| 4,641,636 | | 2/1987 | Cotrel . | |
| 4,815,453 | | 3/1989 | Cotrel . | |
| 5,261,907 | * | 11/1993 | Vignaud et al. | 606/61 |
| 5,534,001 | * | 7/1996 | Schlapfer et al. | 606/61 |
| 5,562,663 | * | 10/1996 | Wisnewski et al. | 606/61 |
| 5,688,272 | * | 11/1997 | Montague et al. | 606/61 |
| 5,725,527 | * | 3/1998 | Biedermann et al. | 606/61 |

* cited by examiner

Primary Examiner—Henry J. Recla
Assistant Examiner—(Jackie) Tan-Uyen T. Ho
(74) Attorney, Agent, or Firm—Nixon & Vanderhye P.C.

(57) ABSTRACT

An apparatus for fixing the spine, and particularly to a spine fixing apparatus for fixing an unstable spine, caused by a fracture or a disease, to be properly collaborated together such that the spine can recover its stable state. The spine fixing apparatus comprising a plurality of spine screw members combined to the spine with a certain distance; a pair of rods detachably combined to the spine screw members, the rods connecting and supporting the spine screw members; pressing members detachably combined to the spine screw members, the pressing member pressing the rod toward the spine screw member; and a connecting device integrally combined to the pressing member, the connecting device flexibly connecting the spine screw members.

9 Claims, 13 Drawing Sheets

SPINE FIXING APPARATUS

BACKGROUND OF THE INVENTION

1. Technical Field

The present invention relates to an apparatus for fixing the spine, and particularly to a spine fixing apparatus for fixing an unstable spine, caused by a fracture or a disease, to be properly collaborated together such that the spine can recover its stable state.

2. Description of the Prior Art

The spine provides a fundamental strength to support a human body, and when the spine is unstable caused by a fracture or a disease, it should be fixed. In order to fix the spine, there have been some methods which employ a unique supporting member or fix the spine integrally with use of screws.

In the method fixing the spine integrally, the screws are combined with the spine at a certain distance and a rod is provided to connect the screws longitudinally. In addition, a pushing plate is mounted on the screw such that the screw can be combined with the rod by pushing the pushing plate. For connecting the rod, a connecting member can also be installed between the rods.

The screw includes a screwing portion combined with the spine and a head portion combined with the rod. Between the screwing portion and the head portion, a neck is formed.

Accordingly, in the conventional spine fixing apparatus, the screw is integrally combined with the rod, and the rods are also integrally connected with use of the connecting member therebetween. In addition, in order to press and connect the rod toward the screw, the pushing plate is separated from the connecting member.

However, the conventional spine fixing apparatus is not sufficient to properly fix the spine because the connecting member cannot adjust its direction as desired.

In addition, the conventional spine fixing apparatus has a disadvantage in that the connecting member cannot adjust its connecting width in order to modify a distance between the rods.

Moreover, in the screw employed in the conventional spine fixing apparatus, the neck has smaller diameter than the head portion, resulting that the neck can be easily broken.

SUMMARY OF THE INVENTION

Therefore, the present invention is designed to overcome the above problems. So, an object of the present invention is to provide a spine fixing apparatus for fixing an unstable spine, caused by a fracture or a disease, to be properly collaborated together such that the spine can recover its stable status.

In order to obtain the above object, the present invention provides a spine fixing apparatus, comprising a plurality of spine screw members combined to the spine with a certain distance; a pair of rods detachably combined to the spine screw members, the rods connecting and supporting the spine screw members; pressing members detachably combined to the spine screw members, the pressing member pressing the rod toward the spine screw member; and a connecting device integrally combined to the pressing member, the connecting device flexibly connecting the spine screw members.

In the spine fixing apparatus, the spine screw member can comprise a screwing portion combined to the spine, the screwing portion having a thread thereon with a certain distance; a hollow head portion including an insert depression for inserting and combining the rod therein, the head portion having an opened end; and a neck integrally formed between the head portion and the screwing portion.

In the spine fixing apparatus, a diameter of the screw portion increases upwardly, and the thread thereof become deeper downwardly.

The spine fixing apparatus can further comprise a hollow screw cap which includes a body having a thread on an inner surface thereof in order to combine with the head portion; and a hollow cap formed integrally with he body, the cap covering the head portion with pressing the pressing member combined with the spine screw member.

In the spine fixing apparatus, the pressing member can comprise a pushing portion for receiving a pressing force by a thread combination of the screw cap; and a pressing portion integrated with the pushing portion for pressing the rod to be fixed with use of a pressing force from the pushing portion, the pressing portion having an insert hole through which the head portion is inserted.

In the spine fixing apparatus, the pressing member can further comprise a guide formed on an outer surface of the pushing portion with a certain size in order to guide the screw cap such that the screw cap combines with the spine screw member without any twist when inserting the screw cap to the spine screw member.

In the spine fixing apparatus, the pressing member can further comprise a guide recess formed on a lower surface of the pressing portion in order to prevent the rod slipped with combining the pressing portion with the rod.

The spine fixing apparatus can further comprise at least one mark formed on an outer surface of the rod such that a bending degree of the rod is easily recognized from outside.

In spine fixing apparatus, the connecting device can comprise combining portions integrally combined with the pressing member; universal joints combined to an insert recess formed on the combining portion, the universal joint being able to rotate freely to every direction; and connecting rods combined with the universal joint, the connecting rod connecting the spine screw member to the head portion.

The spine fixing apparatus can further comprise a length adjusting device connected to the connecting rods for adjusting a distance between the combining portions.

In the spine fixing apparatus, the length adjusting device can comprise a body having a thorough hole through which the connecting rods are movably inserted; and a fixing bolt inserted through an aperture formed on an end surface of the body, the fixing bolt fixing the connected rods, inserted into the thorough hole, at a certain position.

In the spine fixing apparatus, the pressing member can comprise a pushing portion for receiving a pressing force by a thread combination with the screw cap, the pushing portion being in contact with the screw cap; a pressing portion formed on an end of the pushing portion with a certain size, the pressing portion pressing the rod with use of a pressing force from the pushing portion; and a curved surface formed on an end of the pressing portion to have a certain curvature, the curved surface preventing any interference with the rod when the rod is bent.

For obtaining the above object, the present invention also provides a spine fixing apparatus comprising a plurality of spine screw members combined to the spine with a certain distance; a pair of rods detachably combined to the spine screw members, the rods connecting and supporting the spine screw members; and a connecting device detachably combined to the rod, the connecting device connecting a pair of the rods with pressing and fixing the rod toward the spine screw member.

In the spine fixing apparatus, the connecting device can comprise hooked combining portions detachably combined to the rods by such as bolts, the combining portion hooking and fixing the rod; and a connecting member integrated with the combining portion for connecting a pair of the rods.

The spine fixing apparatus can further comprises a length adjusting device for adjusting a connecting distance of the connecting member, wherein the length adjusting device comprises a thread formed on an outer surface of the connecting member, and a length adjusting member having screw holes on both ends, into which the connecting member is inserted.

In the spine fixing apparatus, at least one fixing groove is formed on an outer surface of the length adjusting member, and with use of the fixing groove, the thread of the connecting member and the screw hole of the length adjusting member are pressed and then firmly combined.

In the spine fixing apparatus, the connecting member is formed to be curved with a certain curvature such that the spine disposed between the spine screw members is not interfered therefrom.

In order to acquire the above object, the present invention still further provides a spine fixing apparatus comprising a plurality of spine screw members combined to the spine with a certain distance; a pair of rods detachably combined to the spine screw members, the rods connecting and supporting the spine screw members; pressing members detachably combined to the spine screw members, the pressing member pressing the rod toward the spine screw member; and a connecting device detachably combined with a pair of the rods for adjusting a distance between the rods.

In the spine fixing apparatus, the connecting device can comprise first connecting member detachably combined with one rod, the first connecting member having an extended portion; and second connecting member detachably combined with the other rod, the second connecting member having an upper extended portion and a lower extended portion, wherein the extended portion of the first connecting member is interposed between the upper extended portion and the lower extended portion of the second connecting member, and an interposed width thereof is controllable.

In the spine fixing apparatus, wherein the first and second connecting member include at least one fastening crew; wherein the first connecting member has an opening formed on the extended portion longitudinally, and the second connecting member has at least one thorough hole in the upper and lower extended portion with a certain size; wherein the fastening screw combines the extended portions of the first and second connecting member through the opening of the first connecting member and the thorough hole of the second connecting member; and wherein the fastening screw is movable in the opening of the first connecting member.

In the spine fixing apparatus, the thorough hole of the upper extended portion of the second connecting member is not screwed with the fastening screw, but the thorough hole of the lower extended portion is screwed with the fastening screw.

In the spine fixing apparatus, the first and second connecting members can include fixing screws near the rod for pressing and fixing the rod; wherein the fixing screw is inclined toward the rod at a certain angle.

These and other objects of the present invention will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above object and other advantages of the present invention will become more apparent by describing in detail the preferred embodiment thereof with reference to the attached drawings, in which.

DETAILED DESCRIPTION OF THE PREFERRED EMBODIMENT

Figure 1:
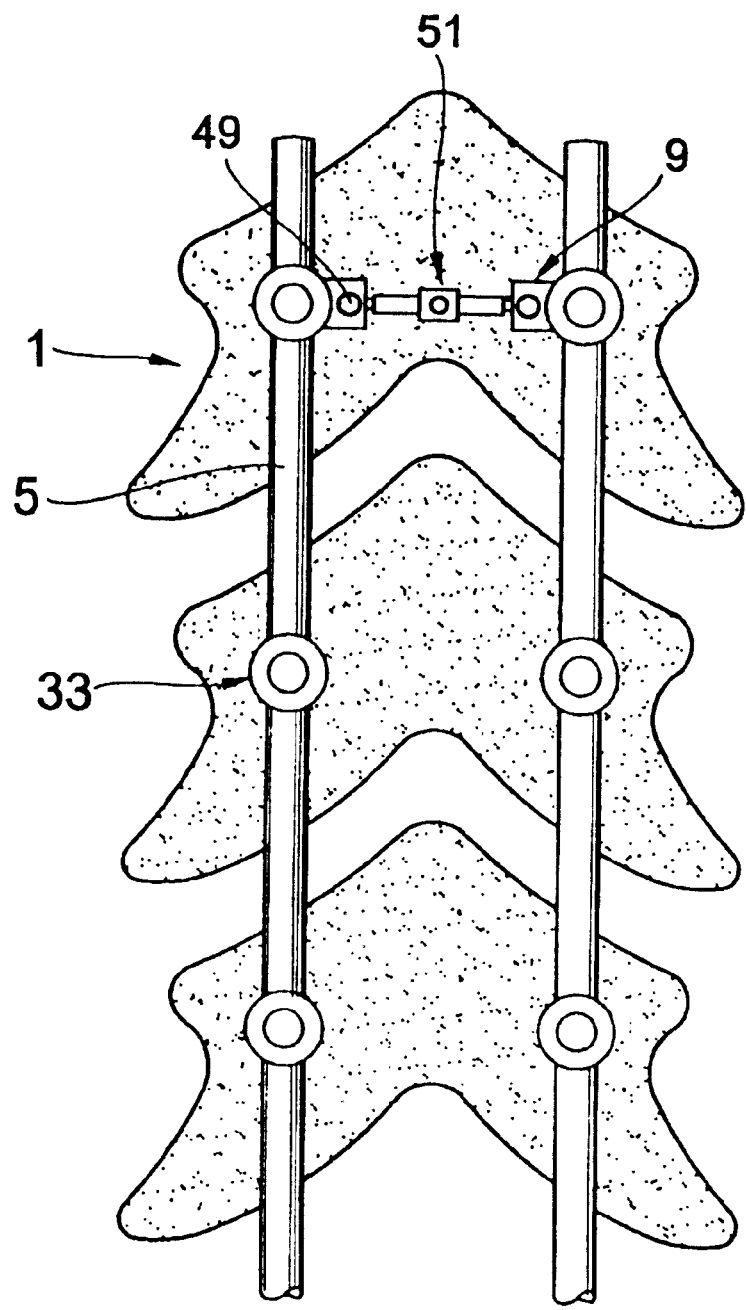
FIG. 1 is a front view showing an application of a spine fixing apparatus is applied according to the first embodiment of the present invention.

Referring to FIG. 1 to FIG. 4, a spine fixing apparatus according to the first embodiment of the present invention is shown. Generally, when the spine 1 is unstable due to a fracture or a disease, the spine fixing apparatus is used for fixing the spine 1 to recover its stable status. As shown in the figures, a plurality of spine screw members are combined to desired positions on the spine 1 with a certain distance. The spine screw members 3 are serially fastened in two rows along the spine 1. The spine screw members 3 fixed to each spine 1 are detachably connected to a pair of rods 5. The rods 5 support and connect the spine screw members 3 in a longitudinal direction of the spine 1. Upon the spine screw member 3, a pressing member 7 is detachably combined. The pressing member 7 acts for pressing the rod 5 toward the spine screw member 3. The rods 5, installed in parallel along the spine 1, are also connected each other by a connecting device 9. In the first embodiment of the present invention, the connecting device 9 is integrally formed with the pressing member 7.

The spine screw member 3 includes a screwing portion 13 for combining with the spine 1, a head portion 19 for combining with the rod 5, and a neck 21 integrally formed between the screwing portion 13 and the head portion 19. At this time, a thread 11 is formed in the screwing portion 13 with a certain distance, and an insert depression 15 is formed in the head portion 19 for inserting the rod 5 therein. The head portion 19 also has a hollow shape with its upper end opened.

The screwing portion 13 preferably has a constant diameter. In addition, it is preferred that depth of the thread 11 is deeper and deeper downwardly such that the screwing portion 13 can be easily inserted into the spine 1, which makes them combined tighter.

Moreover, the pressing member 7 is inserted in and connected to the head portion 19. In that reason, an insert recess 23 is formed on an inner surface of the head portion 19 for insertion of the pressing member 7. The insert recess 23 is recessed on a certain portion on the inner surface of the head portion 19 with a certain depth. On an outer surface of the head portion 19, a thread 25 is formed.

Preferably, diameter of the screw portion 13 and the neck 21 are increased upwardly in order to reinforce its strength. The neck 21 also has a reinforcing portion 27 outwardly rounded on an lower portion of the head portion 19 in order to reinforce its strength.

The spine fixing apparatus of the present invention may further include a screw cap 33 for combining the pressing member 7 with the spine screw member 3. The screw cap 33 includes a body 30 having a thread 29 on its inner surface so as to combine with the thread 25 of the head portion 19 of the spine screw member 3. The screw cap 33 also includes a cap 31 for fixing the pressing member 7. The cap 31 is formed to cover the head portion 19 to prevent the head portion from spreading.

Figure 5:
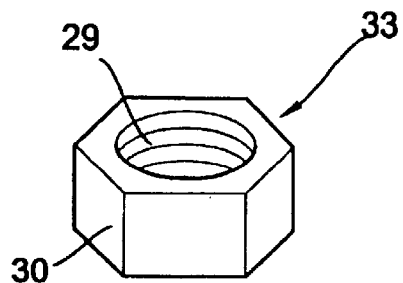
FIG. 5 is a perspective view showing a screw cap according to the first embodiment of the present invention.

In FIG. 5, an example of the screw cap 33 according to the present invention is described. Referring to the figure, the screw cap 33 preferably includes a body 30 in a hollow shape having a thread 29 on its inner surface such that a length of the head portion 19 of the spine screw member 3 and a thickness of the pressing member 7 can be minimized. At this time, the head portion 19 of the spine screw member 3 can be combined through the hollow body 30. The body 30 is preferably formed in a polygon for the purpose of easily combining the screwing portion 13 of the spine screw member 3 into the spine 1.

Figure 2:
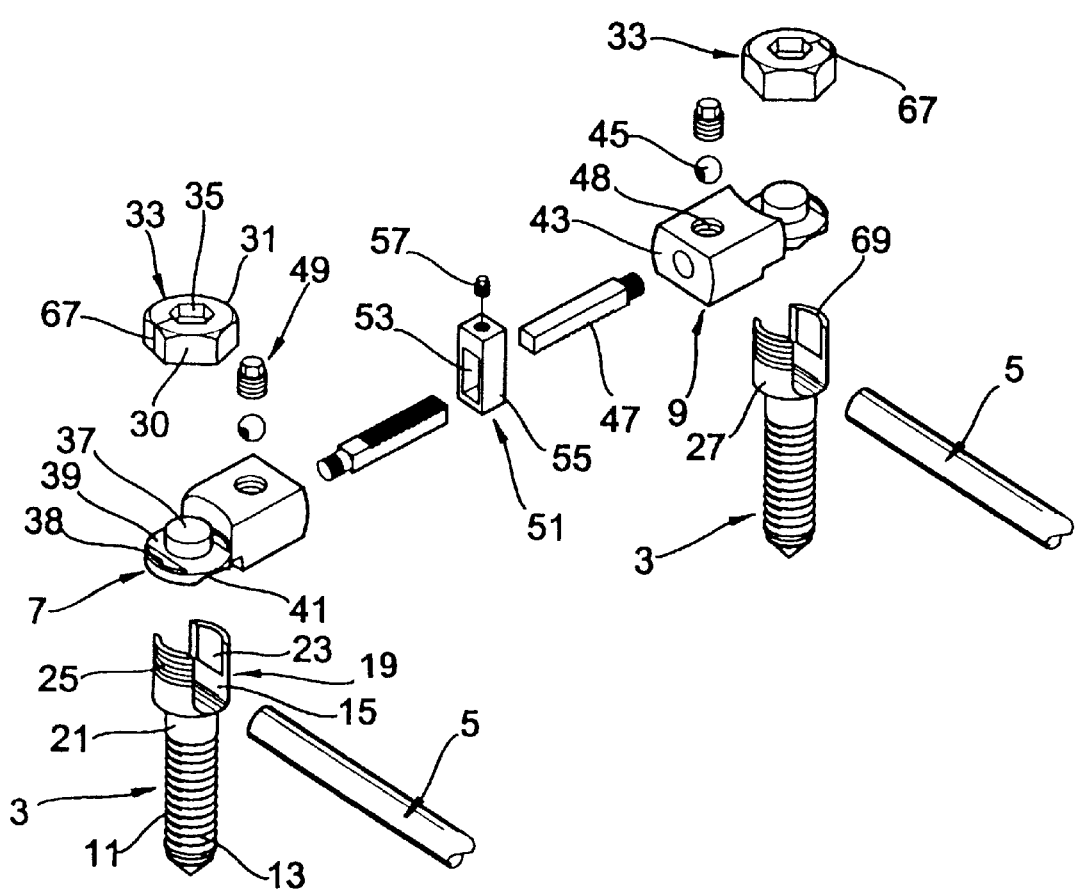
FIG. 2 is an exploded perspective view showing the spine fixing apparatus according to the first embodiment of the present invention.
Figure 3:
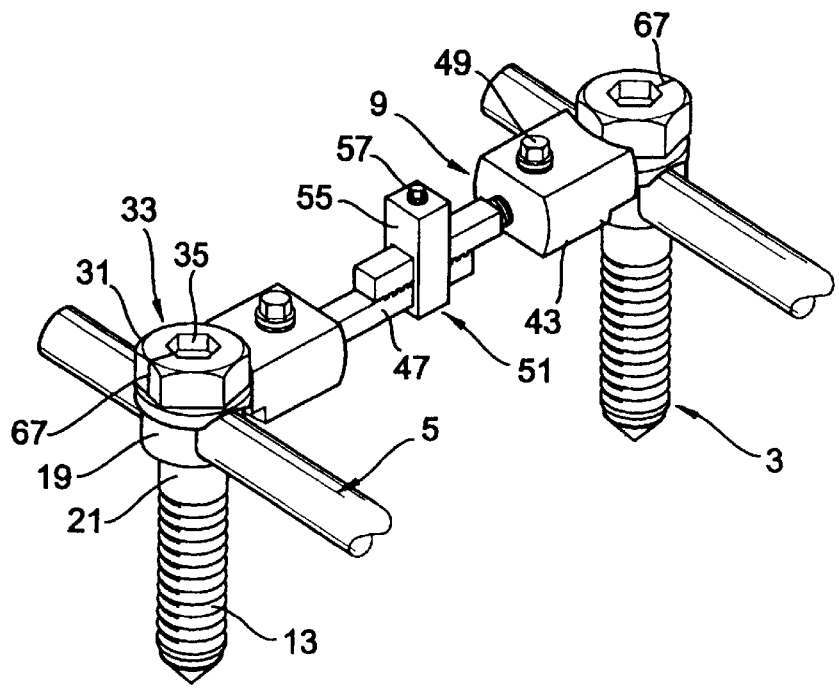
FIG. 3 is a perspective view showing how a spine fixing apparatus is installed according to the first embodiment of the present invention.
Figure 4:
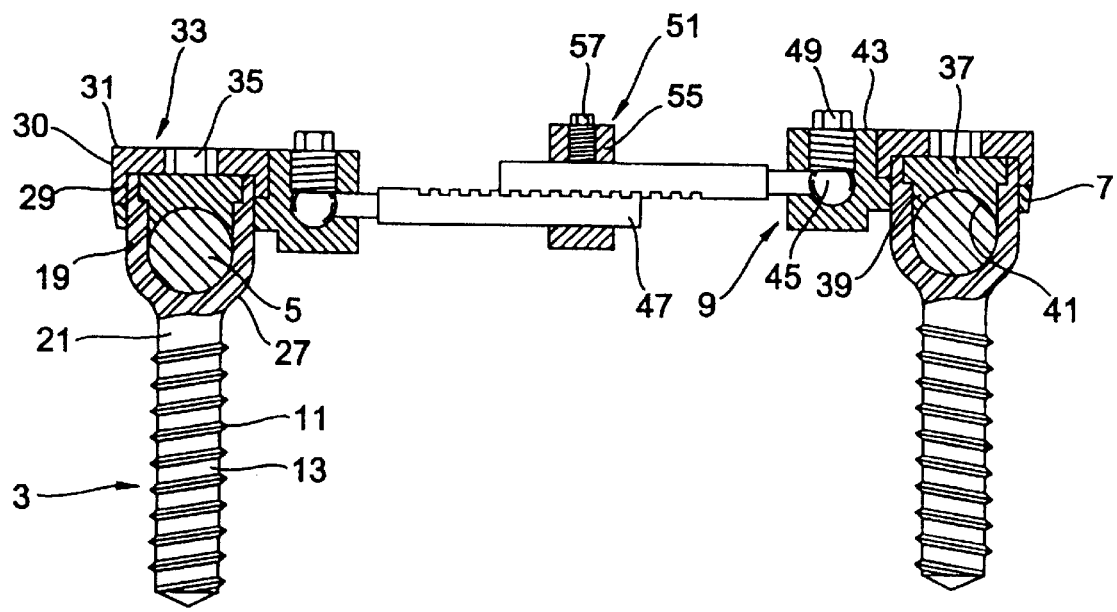
FIG. 4 is a sectional view showing how a spine fixing apparatus is installed according to the first embodiment of the present invention.

Referring to FIG. 2 and FIG. 3 again, on a center of the cap 31, a tightening hole 35 is formed in order to insure a space, required in fixing the screwing portion 13 of the spine screw member 3 to the spine 1 when performing a spine fixing operation. The tightening hole 35, of course, can be formed in various shapes such as tetragon or hexagon.

It is preferred to knurling an outer peripheral surface of the rod 5 such that the rod 5 can be fixed by the pressing member 7 more tightly.

The pressing member 7 includes a cylindrical pushing portion 37 for receiving a pressing force by a thread combination of the screw cap 33, and a pressing portion 39 for fixing the rod 5 with use of a pressing force of the pushing portion 37. At this time, it is preferable that the pressing portion 39 is integrally formed with the pushing portion 37, and has an insert hole 38 through which the head portion 19 of the spine screw member 3 can be inserted. In addition, the pushing portion 37 and the pressing portion 39 is preferably integrally formed.

Figure 6:
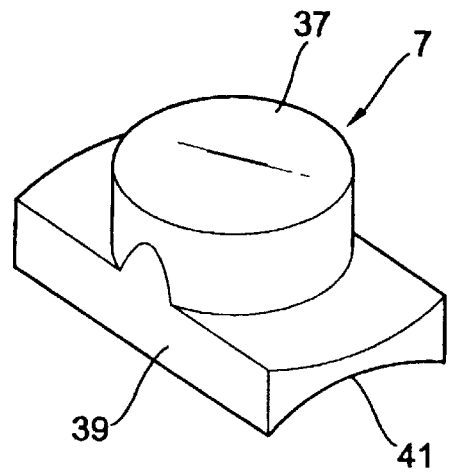
FIG. 6 is a perspective view showing a pressing member according to the first embodiment of the present invention.

Furthermore, though FIG. 2 shows that the pressing member 7 is connected to the connecting device 9, the present invention is not limited to the drawing. As an example, FIG. 6 shows a pressing member 7 for fixing the rod 5 with not being connected to the connecting device 9. In such example, the pressing member 7 includes a cylindrical pushing portion 37 for receiving a pressing force by a thread combination of the screw cap 33, and a pressing portion 39 integrally formed with the pushing portion 37 so as to fix the rod 5 with use of a pressing force from the pushing portion 37.

Referring to FIG. 2 again, the pushing portion 37 is illustrated to be protruded from an end surface of the pressing portion 39. However, not limited to above description, it is also possible to make an end surface of the pressing portion 39 be a pushing portion 37.

On a lower end surface of the pressing portion 39, a guide recess 41 can be formed to be concave with same curvature as the rod 5. Forming the guide recess 41 to have same curvature as the rod 5 makes a contact area increased when combining the pressing portion 39 with the rod 5 and prevents any slip between the pressing portion 39 and the rod 5.

The connecting device 9 includes a combining portion 43 integrated combining with the pressing portion 39. The combining portion 43 has an insert recess through which a universal joint 45 can be mounted to freely rotate. Owing to free rotation of the universal joint 45, although the screwing portions 13 of the spine screw member 3 are not parallel but inclined, the connecting device 9 may flexibly respond to the inclination. A connecting rod 47 is combined to the universal joint 45 with screws. The connecting rod 47 acts for connecting the head portions 19 of the spine screw member 3 to each other.

A control bolt 49 can be provided to an aperture 48 formed in the combining portion 43. The control bolt 49 can adjust a joining degree of the universal joint 45 installed to the combining portion 43.

It is preferred to provide a knurling on outer surface of the universal joint 45 in order to be tightly fixed by the control bolt 49.

The present invention may further include a length adjusting device 51 mounted to the connecting rod 47 for adjusting a distance between the combining portions 43. At this time, the length adjusting device 51 adjusts a distance between the combining portions 43 of the connecting device 9 according to a distance between the spine screw member 3 combined with the spine 1.

The length adjusting device 51 includes a body 55 for inserting the connecting rod 47 therein and a fixing bolt 57 for fixing the connecting rod 47 to a certain position. The body 55 has a thorough hole 53 in which the connecting rod 47 can be inserted and moved. In addition, an aperture is formed on one end surface of the body 55, for example an upper surface, such that the fixing bolt 57 can be inserted into the aperture.

Figure 7:
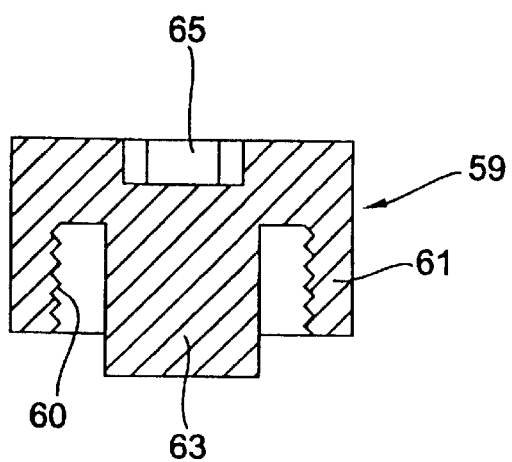
FIG. 7 is a sectional view showing a cap member according to the first embodiment of the present invention.

The pressing member 7 can be separated from the screw cap 33 as shown in FIG. 2, and can be integrated with the screw cap 33 as shown in FIG. 7. In this case, the pressing member 7, integrated with the screw cap 33, can fix the thread 25 of the spine screw member 3 with pressing the rod 5 with the cap member 59.

The cap member 59 in FIG. 7 includes a cap 61 which has a thread on an inner surface in order to combine with the thread 25 of the head portion 19. A pressing portion 63 is formed protrusively on one end of the cap 61 in order to press and fix the rod 5.

The pressing portion 63 is preferably formed to protrude longer than a lower end of the cap 61 in order to tightly fix the rod 5, and more preferably knurled on its surface.

A tightening hole 65 can be formed on a center portion of the cap 61 in order to insure a space, required in fixing the screwing portion 13 of the spine screw member 3 to the spine 1 when performing a spine fixing operation.

In addition, position marks 67, 69 are formed on outer surfaces of the screw cap 33 and the head portion 19 of the spine screw member 3 such that, when combining the head portion 19 and the screw cap 33, they can be not amiss with each other but easily combined. The position marks 67, 69 indicate start positions of their threads respectively.

Now, operation of the spine fixing apparatus of the present invention as constructed above is as follows.

When the spine 1 is unstable by a fracture or a disease, the spine fixing apparatus of the present invention is employed for fixing unstable portion of the spine 1. At this time, the spine 1 is combined with the screwing portion 13 of the spine screw members 3, and the head portions 19 of the spine screw members 3 are connected by the combining portions 43 and the connecting rods 47 of the connecting device 3. In addition, the rod 5 is inserted into the insert depression 15 of the head portion 19, causing it pressed by the pressing portion 39, which is also pressed by the pushing portion 37. The head portion 19 is also pressed by the thread 29 of the screw cap 33 and the pressing portion 37 of the pressing member 7.

In addition, though the screwing portion 13 of the spine screw member 3 is not parallel but inclined in some degree, the universal joint 45 of the connecting device 9 makes it respond flexibly, resulting that the screwing portions 13 of the spine screw members 3 can be suitably fixed according to any angular variation of the spine 1.

At this time, a distance between the combining portions 43 of the connecting device 9 can be adjusted according to a distance between the spine screw member 3 combined with the spine 1 as described below. At first, with the fixing bolts 57 of the length adjusting device 51 loosened, a user moves the connecting rods 47 through the thorough hole 53 to a desired distance. Then, fixing the connecting rods 47 to the thorough hole 53 with use of the fixing bolt 57 makes the distance between the combining portions 43 adjusted easily.

Moreover, adjusting a joining degree of the universal joint 45 can be obtained by rotating the control bolt 49.

Figure 8:
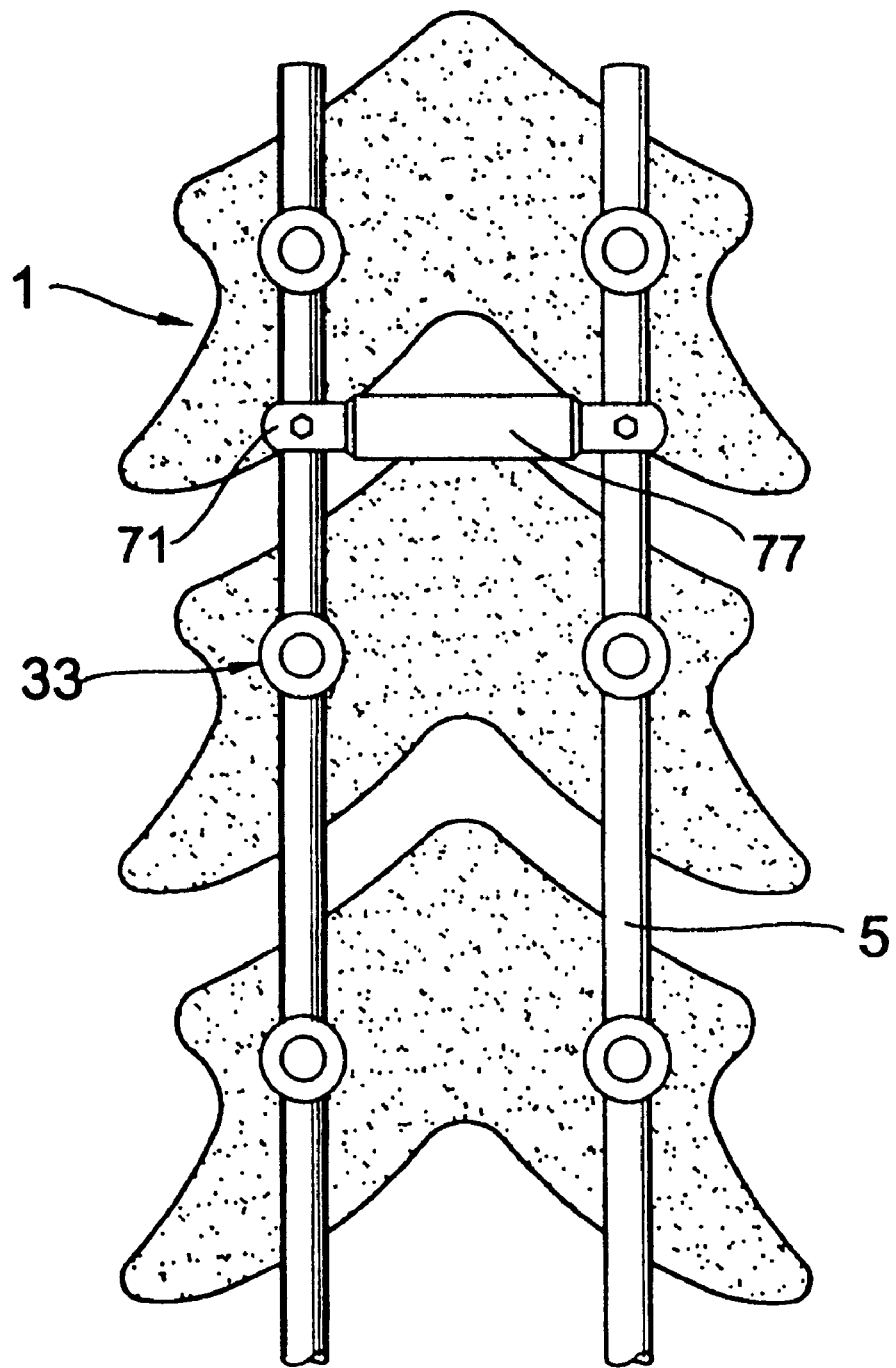
FIG. 8 is a front view showing an application of a spine fixing apparatus according to the second embodiment of the present invention.
Figure 9:
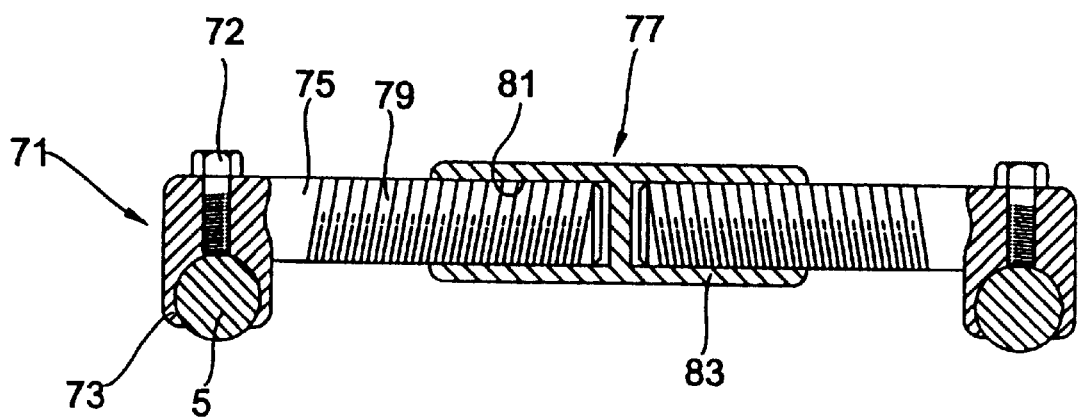
FIG. 9 is a sectional view showing how the spine fixing apparatus is installed according to the second embodiment of the present invention.

FIG. 8 and FIG. 9 show the second embodiment of the present invention. As shown in the figures, in the spine fixing apparatus according to the second embodiment, a plurality of spine screw members 3 are combined to certain portions of the spine 1. The spine screw members 3 are formed serially in two rows along the spine 1, which is identical to the first embodiment. The spine screw members 3 fixed to the spine 1 are detachably connected by a pair of rods 5, which connect and support the spine screw member 3 along the spine 1. A pair of the rods 5, installed along the spine 1 in parallel, are also connected by a connecting device 71 to each other. At this time, the connecting device 71 is detachably combined with the rods 5 and at the same time presses and fixes the rods 5 toward the spine screw member 3.

The connecting device 71 includes a hooked combining member 73 for hooking and combining the rod 5, and a connecting member 75 for connecting the rod 5 with the other adjoining rod. At this time, the connecting device 71 is detachably combined with the rod 5 by such as bolt. The connecting member 75 is extended from the combining member 73 and integrated with the combining member 73.

The combining member 73 is recessed in a certain shape corresponding to a combining position of the rod 5 in order to tightly and easily fix the rod 5, and the combining member 73 is curved in a certain angle.

The connecting device 9 also includes a length adjusting device 77 for adjusting a connecting distance according to a distance between the spine screw members 3 combined with the spine 1.

The length adjusting device 77 includes a length adjusting member 83 into which the connection member 75 can be inserted and with which a thread formed on an outer surface of the connecting member 75 is engaged. The length adjusting member 83 includes screw holes 81 on both ends for combining with the thread 79 formed on the connecting member 75.

Preferably, a certain space should be kept between the screw holes 81 of the length adjusting member 83 for adjusting a connecting distance.

Parts not described in the second embodiment of the present invention are identical to the first embodiment, and not referring them again.

Figure 10:
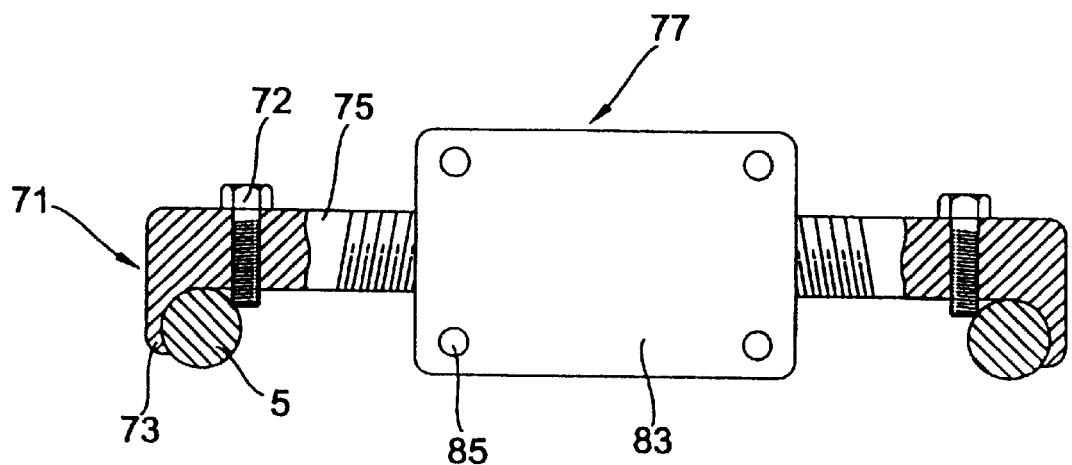
FIG. 10 is a side view showing a spine fixing apparatus according to the third embodiment of the present invention.

FIG. 10 shows the third embodiment of the present invention, which is identical to the second embodiment except the next description.

At least one crimping spat 85 is formed on an outer surface of the above described length adjusting member 83. The crimping spat 85 is required to compress the thread 79 and the screw hole 81 with connecting the connecting member 75 to the length adjusting member 83 such that thread combination between the thread 79 of the connecting member 75 and the screw hole 81 of the length adjusting member 83 can be fixed better.

At this time, the crimping spats 85 preferably have a semispherical shape for easily and tightly compressing the screw hole 81, and are preferably spaced apart from the length adjusting member 83.

On the purpose of that, a user presses the crimping spat 85 with use of separate tools with combining the connecting member 75 to the length adjusting member 83. Then, by a force pressing the crimping spat 85, the screw hole 81 and the thread 79 under the crimping spat 85 are crushed, which accordingly makes combination between the thread 79 and the screw hole 81 more tight.

Figure 11:
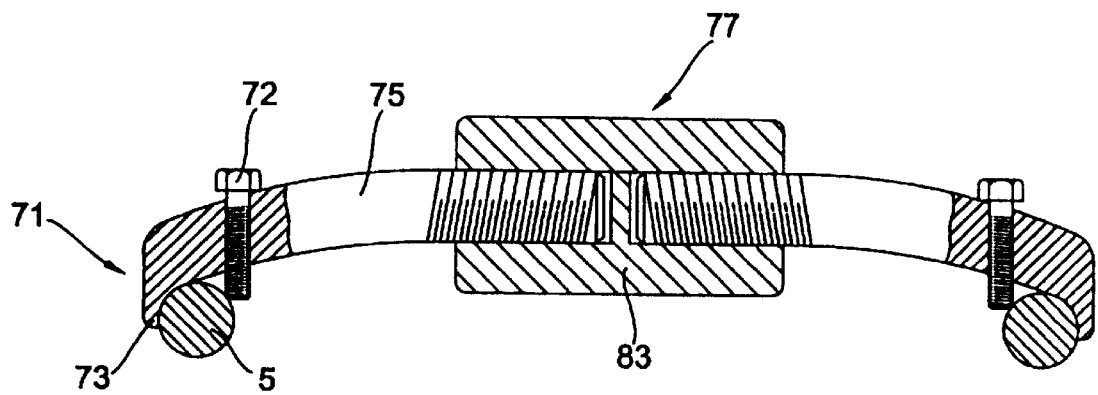
FIG. 11 is a sectional view showing a spine fixing apparatus according to the fourth embodiment of the present invention.

FIG. 11 shows the fourth embodiment of the present invention, which is identical to the second embodiment except the next description.

The connecting member 75 is formed to be curved with a constant curvature such that the spine disposed between a pair of the rods 5 is not interfered thereby.

When the connecting member 75 is connected to the length adjusting device 77, the connecting member 75 is formed to have an arc upwardly from the combining member 73 which is combined with the rod 5 in order that the spine 1 is disposed in a space formed between the rods 5 by way of the arc. Accordingly, the spine 1 is not interfered by the connecting member 75.

FIG. 12 to FIG. 15 show various embodiments of the pressing member 7 of the present invention.

Referring to the figures, the pressing member 7 includes a pushing portion 87 for receiving a pressing force by the screw cap 33, a pressing portion 89 for pressing the rod 5 with use of the pressing force, and a curved surface 91 for preventing any interference with the rod 5 when the rod 5 is bent. The pushing portion 87 is in contact with the screw cap 33 by a thread combination, and receives a pressing force therefrom. The pressing portion 89 is extended from one end of the pushing portion 87 with a certain size so to press the rod 5. The curved surface 91 is formed at an end of the pressing member 89 to have a round with a certain curvature.

Pressing the pressing member 7 toward the rod 5 makes them combined with the rod 5 held down a little by a pressing force. At this time, the curved surface 91 of the pressing member 7 makes the bent rod 5 contact with wider area, more tightly.

The pushing portion 87 preferably has wider area than the pressing portion 89 in order to easily receive a pressing force from the screw cap 33.

Figure 12:
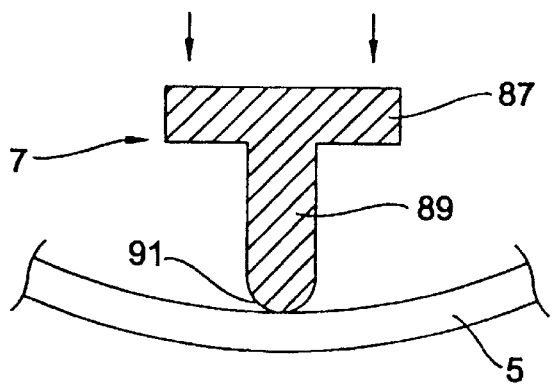
FIG. 12 to FIG. 15 are side views exemplary showing pressing members according to the present invention.
Figure 13:
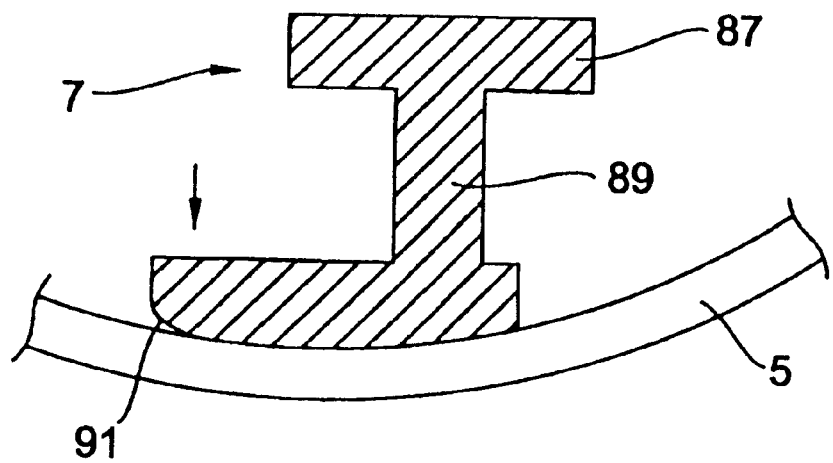
Figure 14:
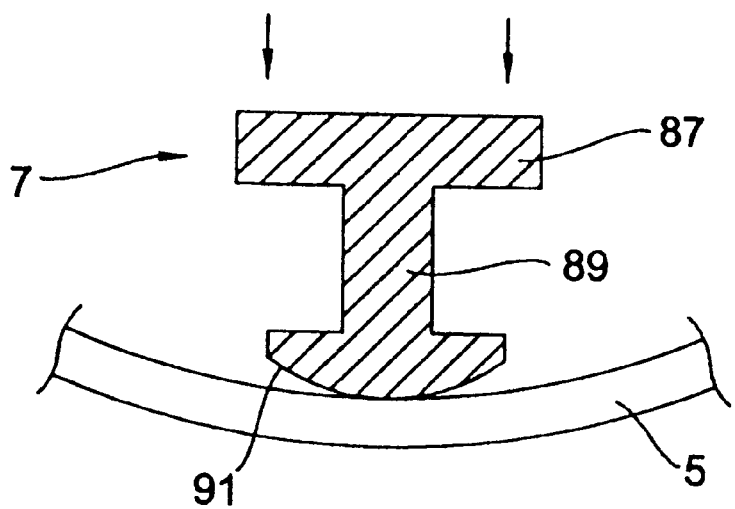
Figure 15:
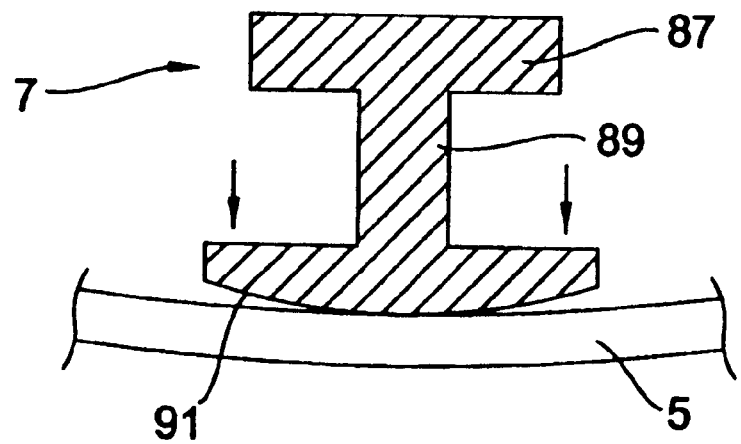

The curved surface 91 can be formed to make a lower end of the pushing portion 87 rounded, as shown in FIG. 12. In addition, as shown in FIG. 13, with forming an extended portion from a lower end of the pushing portion 87, the curved surface 91 can be formed under an end of the extended portion. As shown in FIG. 14 and FIG. 15, with forming an extended portion at a lower end of the pushing portion 87 toward both sides to a certain distance, the curved surface 91 can also be formed at a lower end of the extended portion.

The curved surface 91 formed at a lower end of the extended portion can be either shorter than the pushing portion 87 as shown in FIG. 14 or longer than the pushing portion 87 as shown in FIG. 15.

In such pressing member 7, a pressing force is exerted in the directions shown by arrows in FIG. 12 to FIG. 15. In addition, when the rod 5 is bent by such pressing force, the curved surface 91 formed in a round can prevent any interference with the rod 5 and the pushing portion 87 of the pressing member 7.

Figure 16:
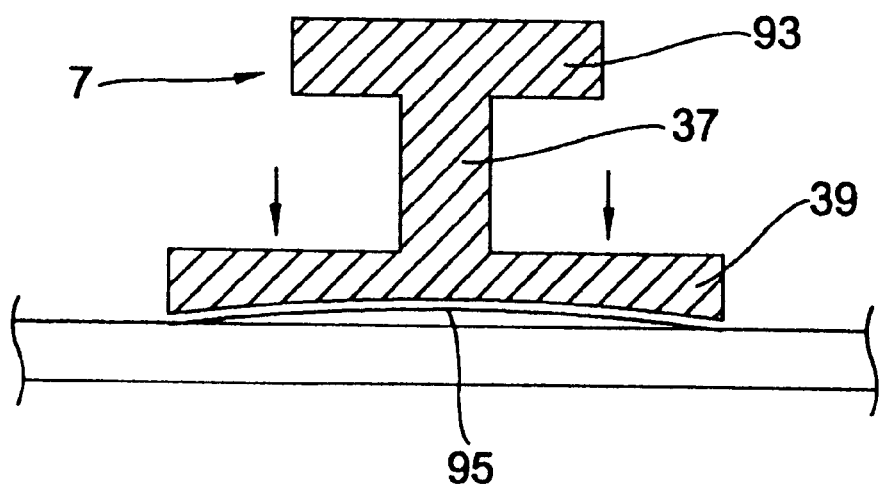
FIG. 16 is a sectional view showing a pressing member according to another embodiment of the present invention.

FIG. 16 shows another embodiment of the pressing member 7 according to the present invention. As shown in the figure, the pressing member 7 can include a guide 93 formed at an upper end of the pushing portion 37 with a certain size laterally. The guide 93 acts for guiding the screw cap 33 to the spine screw member 3 such that the screw cap 33 may combine with the spine screw member 3 without any twist when inserting the screw cap 33 in order to combine the spine screw member 3 with the screw cap 33.

The guide 93 is preferably shorter than the pressing portion 39 such that a pressing force may be transmitted to the pushing portion 37 along a described direction shown by arrows in FIG. 16 and at the same time the screw cap 33 may be easily guided.

On a lower end of the pressing portion 39, a concave can be formed to be depressed inwardly. With combining the rod 5 with the pressing member 7, the concave 95 makes the rod 5 not slipped.

Figure 17:
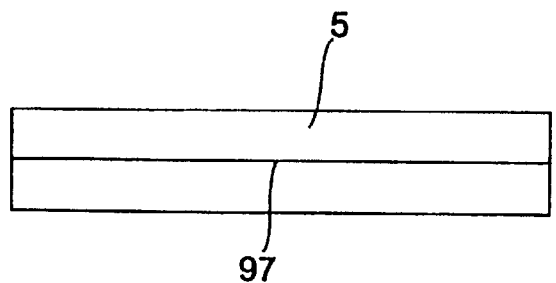
FIG. 17 is a side view showing a rod according to another embodiment of the present invention.
Figure 18:
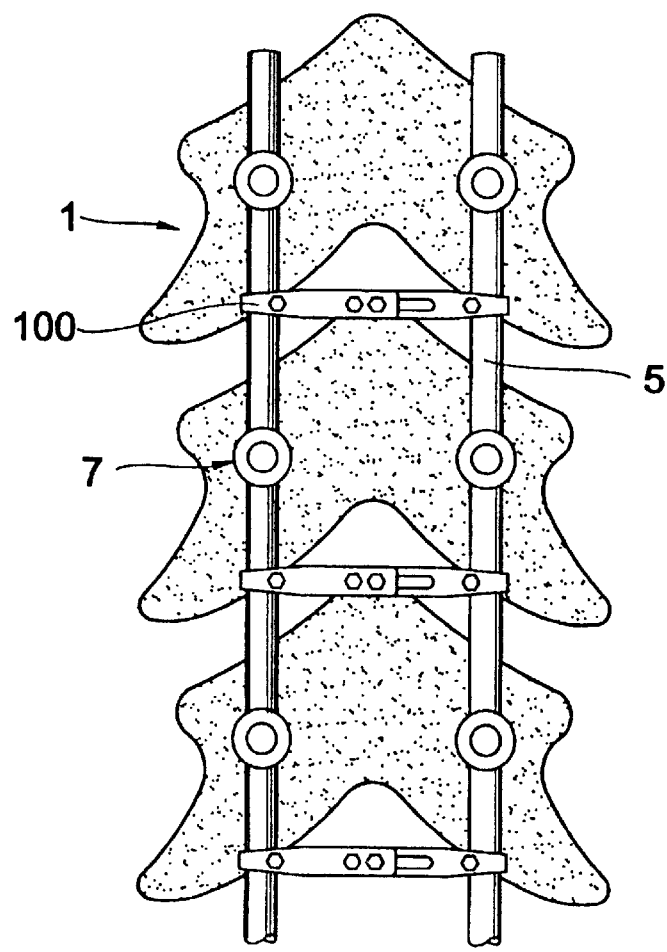
FIG. 18 is a front view for illustrating how a spine fixing apparatus is installed according to still another embodiment of the present invention.
Figure 19:
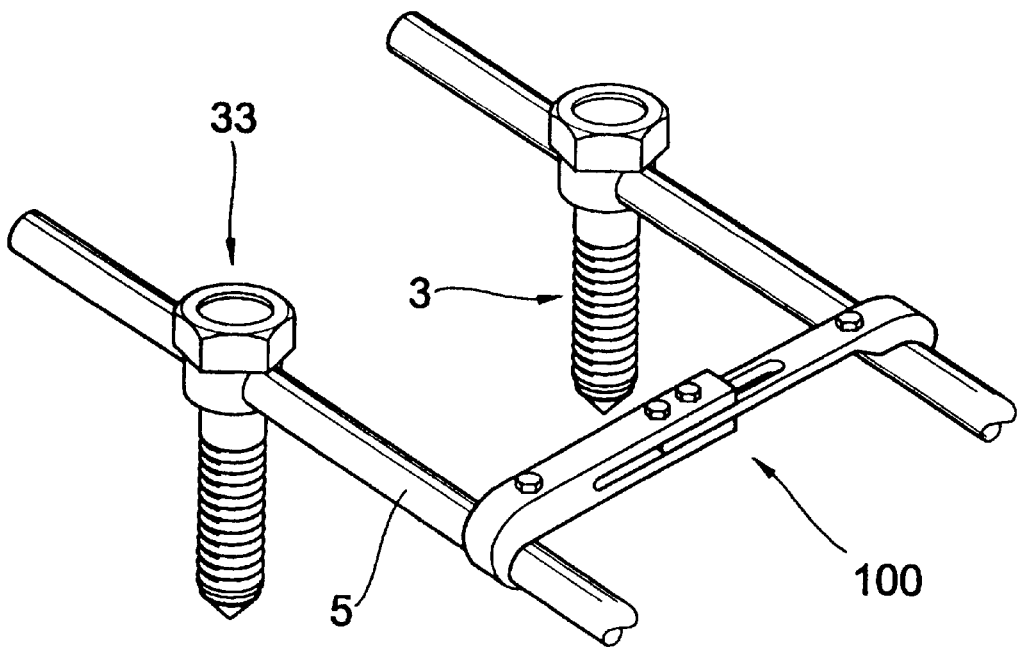
FIG. 19 is a perspective view showing the spine fixing apparatus of FIG. 18.

Referring to FIG. 17 next, shown is a mark 97 for helping to recognize how the rod 5 is bent. At least one mark 97 is provided on an outer surface of the rod 5. The mark 97 is preferably formed along a length of the rod 5 in order to recognize a bending degree of the rod 5 easily from outside. For examples, only one mark 97 can be formed on a peripheral surface of the rod 5, or two marks 97 can be formed by a 180 degrees, or else four by a 90 degrees.

FIG. 18 to FIG. 24 show the spine fixing apparatus according to still another preferred embodiment of the invention. Above mentioned description will not be explained in detail in this embodiment.

Referring to the figures, a plurality of spine screw members are combined into certain portions of the spine 1 with a predetermined interval. Spine screw members 3 are serially formed in two rows along the spine 1. Spine screw members fixed to the spine are connected detachably by a pair of rods 5, which support the spine 1 in a longitudinal direction through the spine screw members 3. A pressing member 7 is installed detachably on the spine screw member 3 in order to press the rod 5 toward the spine screw member 3. The connecting device 100 acts for adjusting a distance between the rods 5. The rods 5 installed along the spine 1 are also connected to adjust a connecting width by a connecting device 100.

Referring to FIG. 20 to FIG. 24, the connecting device 100 roughly includes a first connecting member 110 and a second connecting member 120. One end of the first connecting member 110 is bent inwardly in order to surround a part of the rod 5, and the other end thereof extends toward the other rod. At this time, it is advantageous that the one end of the first connecting member 110 surrounds sufficiently the rod not to be separated, and preferably surrounds the rod 5 approximately 180 degrees.

Besides, the first connecting member 110 has a fixing screw 112 at a little inner position than a vertical center line of the rod 5 for pressing and fixing the rod 5, and a thorough hole 150 through which the fixing screw is inserted and engaged by a thread. In this case, the fixing screw 112 is, preferably, inclined slightly towards the rod 5, and most preferably inclined about 5 degrees. The fixing screw 112 is also preferable to form its end 114, in contact with the rod 5, rounded so that an area contacting with the rod becomes larger for the purpose of more stable combination thereof.

Figure 23:
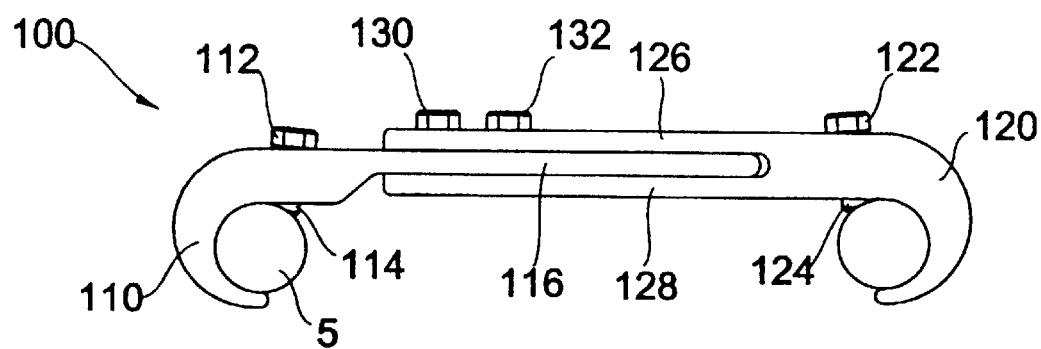
FIG. 23 is a front view showing a combination of the first and second connecting members of the spine fixing apparatus of FIG. 18.
Figure 24:
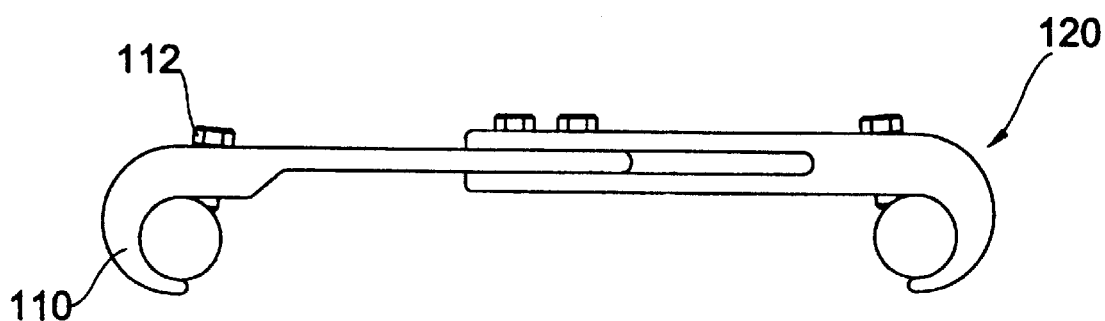
FIG. 24 is a another combination of the first and the second connecting members of the spine fixing apparatus of FIG. 18.

Referring to FIG. 23, the first connecting member 110 is formed to have a thickest portion above the rod 5, and to become thinner with surrounding the rod 5. At this time, it is structurally preferable that an end portion of the first connecting member 110, which surrounds the rod 5, is terminated roundly since it facilitate the rod 5 to be joined therein. In the first connecting member 110, the thickness above the rod 5 is maintained to a joint position of the fixing screw 112, and beyond the position the bottom face thereof is rising for the width to decrease drastically passing over the joint position. Then, the first connecting member 110 has the extended portion 116 extending toward the other rod with its width narrowed.

Figure 20:
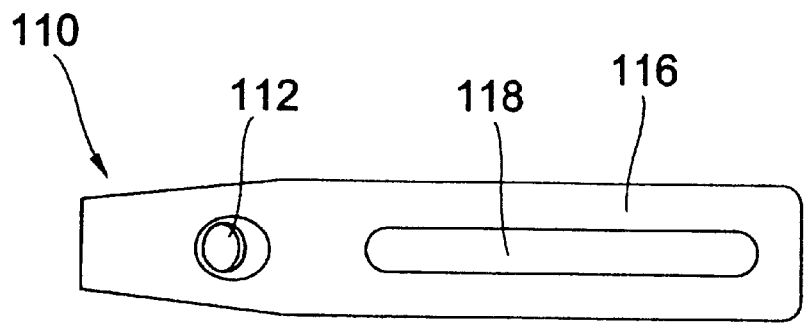
FIG. 20 is a plan view showing a first connecting member of a connecting device of the spine fixing apparatus of FIG. 18.
Figure 21:
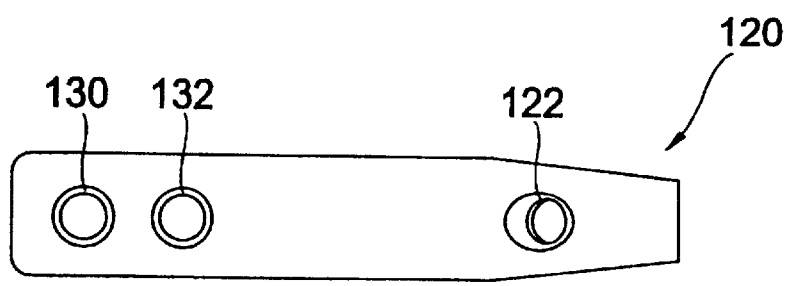
FIG. 21 is a plan view showing a second connecting member of a that a connecting width of the connecting device of the spine fixing apparatus of FIG. 18.
Figure 22:
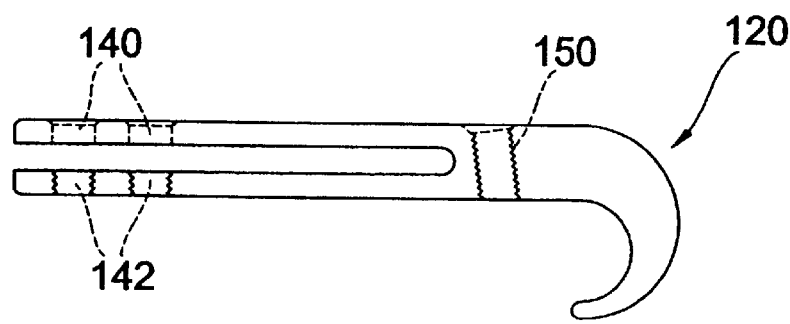
FIG. 22 is a front view showing the second a first connecting member of the spine fixing apparatus of FIG. 18.

The first connecting member has an opening 118 formed on the extended portion 116 longitudinally, that is well shown in FIG. 20 illustrating the plan view of the first connecting member 110. The opening 118 of the first connecting member 110 preferably has a width approximately the same as one third of the extended portion 116. Preferably, end of the opening 118 is formed in a semicircle.

The second connecting member 120 is formed approximately opposite to the first connecting member 110. A portion thereof connected with the rod 5 is identical to that of the first connecting member 110, however an upper surface of the second connecting member 120 is formed a little higher than that of the first connecting member 110. A fixing screw 122 is installed on the second connecting member 120, similar to the first connecting member 110. However, the fixing screw part 122 of the second connecting member 120 is formed longer so that it may correspond to the width of the second connecting member 120. The fixing screw 122 of the second connecting member 120 also preferably has its end 124, in contact with the rod 5, rounded, similar to the fixing screw 112 of the first connecting member 110.

The second connecting member 120 also is extended toward the rod 5 combined with the first connecting member 110. At this time, the extended part of the second connecting member 120 includes an upper extended portion 126 and a lower extended portion 128, both of which are spaced apart up and down each other. The extended portion 116 of the first connecting member 110 is inserted into this space. In this case, it is preferred that the extended portion 116 of the first connecting member 110 and the upper and lower extended portions 126, 128 of the second connecting member 120 are formed to have same thickness.

Thorough holes 140, 142 are formed at the same position on the upper and lower extended portions 126, 128 of the second connecting member 120, and fastening screws 130, 132 are joined through the thorough hole 140, 142. At this time, a thread is not formed in the thorough hole 140 of the upper extended portion 126, but a thread is formed in the thorough hole 142 of the lower extended portion 128 such that the fastening screws 130, 132 cannot be screwed with the upper extended portion 126 but screwed with the lower extended portion 128. Accordingly, when screwing the fastening screws 130, 132, the upper extended part 126 keeps its position, but the lower extended portion 128 is raised upward by the fastening screws 130, 132 such that the extended portions 126, 128 of the second connecting member 120 get close together with the extended portion 116 of the first connecting member 110. In this case, the thorough hole 140 of the upper extended portion 126 has preferably a little larger diameter than the thorough hole 142 of the lower extended portion 128.

In this case, the fastening screws 130, 132 join together the thorough holes 140, 142 of the second connecting member 120 through the opening 118 of the first connecting member 110. Therefore, owing that the opening 118 of the first connecting member 110 is formed lengthy, when joining the extended portions 116, 126, 128 all together by the fastening screws 130, 132, a user can adjust their interposed width by moving the fastening screws 130, 132 through the opening 118 of the first connecting member 110. Such adjustment of the interposed width can be performed easily by way that a user engages the fastening screws 130, 132 with the lower extended portion 128 of the second connecting member 120 in a little degree through the opening 118 of the first connecting member, and then engaging them fully after adjusting the interposed width.

At this time, one or more fastening screws can be used, though in the invention two screws are used in consideration of a structural stability and a manufacturing convenience.

In addition, it is preferred that widths of the first and second connecting members 110, 120 are bigger at the extended portions 116, 126, 128, decreased gradually at a region where combining with the rod 5, and then getting slightly wider with surrounding the rod 5. This is intended for the connecting device to be structurally robust and stable by getting larger its contacting area at the joint position between the extended portions 116, 126, 128 and at its combining position with the rod 5, that allows the width thereof being reduced in some degree at an area having relatively less stress.

As constructed above, the spine fixing apparatus according to the present invention has an effect to recover the spine to the stable state by fixing it properly with the connecting device connected to the spine screw members when the spine is unstable because of a fracture or related disease.

Besides, the present invention has an advantage that it is structurally quite stable, by screwing securely the connecting members one another using the fastening screws, and joining rods closely using the fixing screws.

Furthermore, it has another advantages that it is easy to combine the connecting member with the rod by joining with the rod using the fixing screws and convenient in manufacturing and utilization by simplifying the structure.

The spine fixing apparatus according to the present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A spine fixing apparatus comprising:
   a) a plurality of spine screw members securable to the spine at spaced apart locations, each spine screw member including:
      a screwing portion securable to the spine and having a thread thereon;
      a hollow head portion including an insert depression, an open end, and a thread formed on an outer surface thereof; and
      a neck integrally formed between the hollow head portion and the screwing portion;
   b) a pair of rods received in the insert depression of the hollow head portion and detachably securable to the spine screw members, the rods connecting and supporting the spine screw members;
   c) a plurality of pressing members detachably securable to the spine screw members, each pressing member pressing the rod toward the spine screw member;
   d) a connecting device integrally formed with the pressing member and adjustably connecting the spine screw members; and
   e) a hollow screw cap including:
      a hollow body having a thread on an inner surface thereof in order to engage with the thread formed on the outer surface of the hollow head portion of the spine screw member, the hollow screw cap covering the hollow head portion while pressing the pressing member combined with the spine screw member.

2. A spine fixing apparatus as claimed in claim 1, wherein the pressing member comprises:

a pushing portion for receiving pressing force by a thread combination of the hollow screw cap; and a pressing portion integrated with the pushing portion for pressing the rod to be fixed by the pressing force from the pushing portion, the pressing portion having an insert hole through which the hollow head portion is inserted.

3. A spine fixing apparatus as claimed in claim 2, wherein the pressing member further comprises a guide formed on an outer surface of the pushing portion with a certain size in order to guide the hollow screw cap such that the hollow screw cap combines with the spine screw member without any twist when fitting the hollow screw cap into the spine screw member.

4. A spine fixing apparatus as claimed in claim 2, wherein the pressing member further comprises a guide recess formed on a lower surface of the pressing portion in order to prevent the rod from slipping when the pressing portion is in combination with the rod.

5. A spine apparatus as claimed in claim 1, further comprising at least one mark formed on an outer surface of the rod such that a bending degree of the rod is easily recognized from outside.

6. A spine fixing apparatus as claimed in claim 1, wherein the connecting device comprises:

combining portions integrally formed with the pressing member;

universal joints combined to an insert recess formed on the combining portion, the universal joint being able to rotate freely in every direction; and connecting rods combined with the universal joint, each connecting rod connecting the hollow head portions of the spine screw members.

7. A spine fixing apparatus as claimed in claim 6, further comprising a length adjusting device connected to the connecting rods for adjusting a distance between the combining portions.

8. A spine fixing apparatus as claimed in claim 7, wherein the length adjusting device comprises:

a body having a thorough hole through which the connecting rods are movably inserted; and a fixing bolt inserted through an aperture formed on an end surface of the body, the fixing bolt securely fixing the connected rods inserted into the through hole at a certain position.

9. A spine fixing apparatus as claimed in claim 1, wherein the pressing member comprises:

a pushing portion for receiving pressing force by a thread combination with the hollow screw cap, the pushing portion being in contact with the hollow screw cap;

a pressing portion formed on an end of the pushing portion with a certain size, the pressing portion pressing the rod with the pressing force from the pushing portion; and a curved surface formed on an end of the pressing portion to have a certain curvature, the curved surface preventing any interference with the rod when the rod is bent.

* * * * *